United States Patent [19]
Kieturakis et al.

[11] Patent Number: 5,403,336
[45] Date of Patent: Apr. 4, 1995

[54] SKIN SEAL DEVICE AND ASSEMBLY THEREOF

[75] Inventors: Maciej J. Kieturakis, San Carlos; Helmut L. Kayan, Redwood City, both of Calif.

[73] Assignee: General Surgical Innovations, Inc., Portola Valley, Calif.

[21] Appl. No.: 236,370

[22] Filed: Apr. 29, 1994

Related U.S. Application Data

[63] Continuation-in-part of Ser. No. 124,333, Sep. 20, 1993, abandoned.

[51] Int. Cl.⁶ .......................................... A61M 5/00
[52] U.S. Cl. .............................. 606/167; 606/164
[58] Field of Search ............ 604/164, 165, 167, 174, 604/175, 178; 606/167, 191, 198; 128/20, DIG. 26; 411/395, 399, 411, 424, 426

[56] References Cited

U.S. PATENT DOCUMENTS

| | | | |
|---|---|---|---|
| 2,437,381 | 3/1948 | Cullen | 606/191 |
| 4,491,126 | 1/1985 | Cullor | 604/175 |
| 4,772,261 | 9/1988 | Von Hoff et al. | 604/175 |
| 4,826,487 | 5/1989 | Winter | 604/175 |
| 5,009,643 | 4/1991 | Reich et al. | |
| 5,112,321 | 5/1992 | Hiltebrandt | 604/167 |
| 5,217,441 | 6/1993 | Shichman | 604/164 |
| 5,226,890 | 7/1993 | Ianniruberto et al. | 604/174 |
| 5,252,016 | 10/1993 | Schmid et al. | 411/426 |
| 5,257,973 | 11/1993 | Villasuso | 604/175 |

FOREIGN PATENT DOCUMENTS

| | | | |
|---|---|---|---|
| 4121751 | 1/1993 | Germany | 411/424 |
| 2019219 | 10/1979 | United Kingdom | 604/174 |

Primary Examiner—Stephen C. Pellegrino
Assistant Examiner—Nancy Mulcare
Attorney, Agent, or Firm—Flehr, Hohbach, Test, Albritton & Herbert

[57] ABSTRACT

A skin seal for making a substantially gas-tight seal with the skin of a patient having a wall with an incision therein comprising a body having proximal and distal extremities and having a flow passage extending from the proximal to the distal extremity. The body has a first outer cylindrical surface extending from the distal extremity toward the proximal extremity and has a uniform diameter. The body also has a second outer tapered surface extending from the first surface toward the proximal extremity and has a gradually increasing diameter. A helical thread is formed on the first and second outer surfaces.

5 Claims, 1 Drawing Sheet

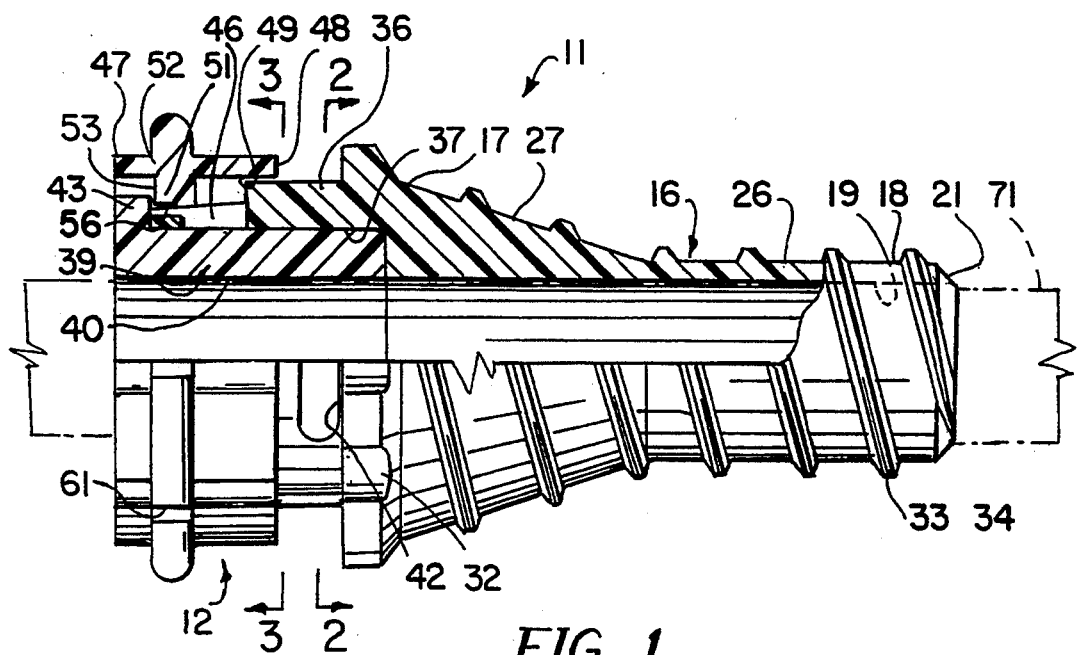
FIG. 1
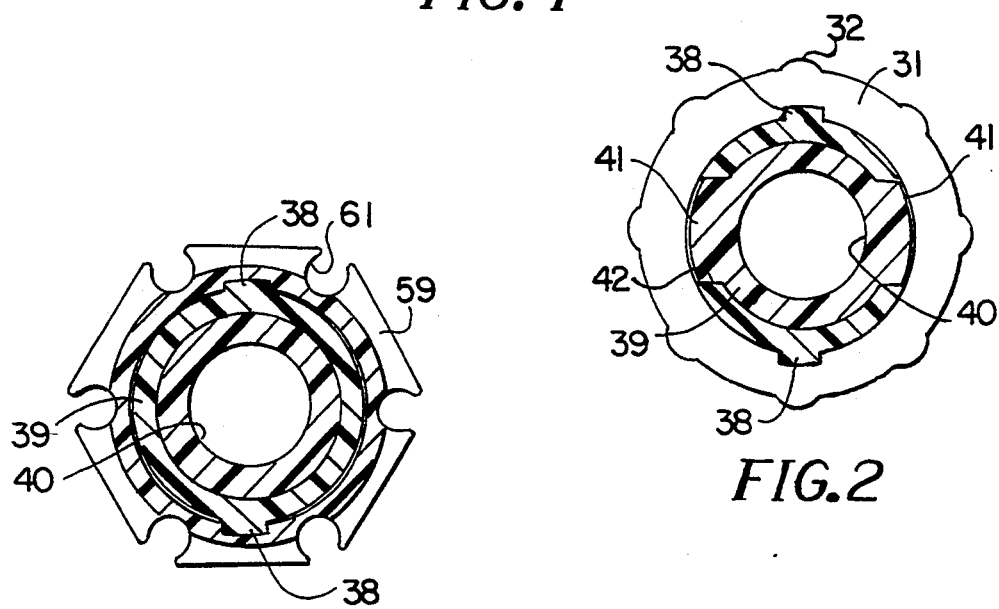
FIG. 2
FIG. 3
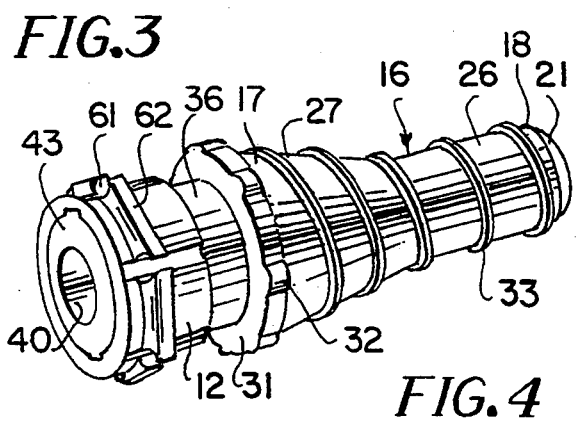
FIG. 4

SKIN SEAL DEVICE AND ASSEMBLY THEREOF

This application which is a continuation-in-part of Ser. No. 08/124,333, filed on Sep. 20, 1993, which is abandoned.

This invention relates to a skin seal device and assembly thereof.

Skin seals have heretofore been provided for use in surgical procedures for forming a seal between introducers and the skin of the patient to provide a substantially gas-tight seal therebetween. Typically, such skin seals have been designed for use with incisions having a length of approximately one centimeter. Certain surgeons have found it desirable to utilize incisions which have a length greater than one centimeter which makes it difficult to form the proper seal with the conventional skin seals making it necessary for the surgeon to suture at least a part of the incision to form the seal. There is therefore need for new and improved skin seal and assembly thereof which can be utilized with incisions of various lengths.

In general, it is an object of the present invention to provide a skin seal device and assembly thereof which can be utilized with incisions of various lengths.

Another object of the invention is to provide a skin seal device and assembly thereof which makes it possible to form a substantially gas-tight seal with incisions of various lengths.

Additional objects and features of the invention will appear from the following description which the preferred embodiments set forth in detail in conjunction with the accompanying drawing.

FIG. 1 is a side elevational view of a skin seal and assembly thereof incorporating the present invention.

FIG. 2 is a cross-sectional view taken along the line 2—2 of FIG. 1.

FIG. 3 is a cross-sectional view taken along the line 3—3 of FIG. 1.

FIG. 4 is an isometric view of the skin seal and assembly thereof shown in FIGS. 1–3.

In general, the skin seal device of the present invention is utilized for making a substantially gas-tight seal with the skin of a patient having a wall with an incision therein. It is comprised of a body having proximal and distal extremities and having a flow passage extending from the proximal to the distal extremity. The body has a first cylindrical outer surface extending from the distal extremity toward the proximal extremity of a substantially uniform diameter and a second outer surface extending from the first outer surface toward the proximal extremity. A substantially continuous helical thread is formed on the first and second surfaces whereby when the skin seal is rotated, the screw threads will penetrate into a incision and will continue to be threaded it into the incision as the skin seal is rotated until a substantially gas-tight seal is formed with the skin surrounding the incision.

More in particular as shown in the drawings, the skin seal and the assembly thereof consists of a skin seal device 11 and a collar 24 mounted thereon. The skin seal and collar are formed of a suitable plastic material such as a polycarbonate or polysulfone. It consists of an integral body 16 which is provided with proximal and distal extremities 17 and 18 and having a flow passage 19 extending from the proximal extremity 17 to the distal extremity 18. The flow passage is sized to a particular size, as for example a diameter of 0.475 inches which is adapted to receive a conventional introducer or like medical device to be inserted therethrough. The distal extremity of the body is provided with a chamfer 21 of a suitable angle, as for example an angle of 30° from a line parallel to the longitudinal axis of the flow passage 19.

The body 16 is provided with a first outer cylindrical surface 26 which can have a suitable outside diameter, as for example 0.550 inches and be of a suitable length, as for example one inch which extends from the distal extremity to slightly greater than one-half the distance to the proximal extremity where it adjoins a second outer tapered surface 27 which gradually increases in diameter in a direction towards the proximal extremity 17. A suitable taper ranging from 15° to 30° can be provided. The proximal extremity 17 adjoins a cylindrical shoulder 31 having circumferentially spaced-apart protrusions 32 thereon. A helical thread 33 is formed integral with the body on the first and second outer surfaces 26 and 27 and is continuous from the distal extremity 18 to the proximal extremity 17 where it terminates. The thread 33 is provided with a tapered commencement point 34 at a point immediately adjacent the distal extremity of the chamfer 21 and extends over the chamfer 21. The thread 33 has a conventional configuration in cross section. The helical thread 33 can have a certain density, as for example four threads per inch with the same number of threads per inch for the first outer cylindrical surface and the second outer tapered surface without a discontinuity.

The body 16 is also provided with a cylindrical portion 36 which is provided with a cylindrical recess 37 of a greater diameter than the diameter of the bore 19 and is coaxial with the bore 19. The cylindrical portion 36 is provided with a pair of diametrically opposed outwardly extending protrusions 38 (see FIG. 3). A resilient insert 39 is mounted in the recess 37 and has a bore 40 in registration with the passage 19. The insert 39 is provided with radially extending ears 41 that extend through slots 42 and serve to retain the insert 39 within the recess 37. A slotted collet 46 extends over the insert 39 and is slidably engaged by the collar 12. The collet 46 is retained on the insert 39 by a flange 43 formed integral with the insert 39.

The collar 12 consists of a body 52 also formed of a plastic polycarbonate material and has proximal and distal extremities 47 and 48. The body 46 is provided with a bore 49 which extends from the proximal extremity to the distal extremity 48. The body is provided with an inwardly extending flange 51 which extends into the bore 49 and has a surface 53 which extends in a direction perpendicular to the axis of the bore 49 which is adapted to engage the flange 43 and to retain the collar 12 over the collet 46. The flange 51 is provided with a cam surface 56 adapted to engage the slotted collet 46 to cause the insert 39 to move between retaining and releasing positions.

The body 56 is also provided with an outwardly extending annular shoulder 59 having circumferentially spaced-apart arcuate recesses 61 therein extending parallel to the longitudinal axis of the bore 49.

Operation and use of the skin seal device and the assembly thereof may now be briefly described as follows. Let it be assumed that it is desired to perform a laparoscopic procedure in which an incision is to be made in the abdominal wall of the patient. Let it also be assumed that the incision is greater than the conventional one centimeter length incision. Let it also be assumed that it is desired to introduce a medical device such as an introducer 71 through the incision. The skin seal 11 of the present invention with the collar 12 mounted thereon is passed over the introducer 71. The introducer 71 with the skin seal 11 thereon is introduced through the incision to bring the distal extremity 18 into engagement with the incision. The shoulder 31 is then grasped by the fingers of the hand and pushed slightly downwardly and rotated to cause the helical thread 33 to penetrate the incision and engage the skin surrounding the incision. It is thereafter rotated to cause the thread 33 to engage the abdominal wall through which the incision has been made and the skin covering the wall to gradually advance the skin seal inwardly of the incision. Since the thread 33 commences on the taper 21 it is very easy to start the thread 33 into the incision and to cause the skin seal 11 to advance into the incision. For a small one centimeter incision, the helical thread 33 on the first outer cylindrical surface 26 normally is sufficient to form a gas-tight seal with the skin of the patient. However, in the event of a larger or longer incision it is merely necessary to continue rotation of the skin seal 11 to further threadedly advance the skin seal into the incision to cause the second outer tapered surface 27 to enter the incision. Such advancement is continued until the tapered surface 27 is entered far enough to form a gas-tight skin seal with the skin of the patient. Thus, it can be seen with the skin seal of the present invention it is possible to obtain gas-tight seals with incisions of the various lengths, as for example a range from one centimeter to three centimeters without difficulty.

The collar 12 can be moved to clamp the introducer 71 in the desired position as described in copending application, Ser. No. 07/968,201, filed Oct. 29, 1992. When the medical procedure for which the introducer 71 was utilized has been completed, the introducer 71 and the skin seal 11 can be removed by rotating the shoulder 31 in the opposite direction to cause the skin seal 11 and the introducer carried thereby to be removed from the incision after which the incision can be closed in a conventional manner, as for example by sutures.

In view of the foregoing, it can be seen that there has been provided a skin seal and assembly thereof which makes it possible to form skin tight seals in incisions of various lengths in excess of one centimeter.

What is claimed is:

1. A skin seal device for making a substantially gas-tight seal with the skin of a patient having a wall with an incision therein comprising an integral body having proximal and distal extremities and having a flow passage extending from the proximal to the distal extremity, said body having a first outer cylindrical surface extending from the distal extremity toward the proximal extremity and having a uniform diameter and a second outer tapered surface extending from the first outer cylindrical surface toward the proximal extremity and having a gradually increasing diameter and a continuous helical thread of the same number of threads per inch for the first outer cylindrical surface and the second outer tapered surface without a discontinuity formed on the first and second outer surfaces extending from the distal extremity towards the proximal extremity, the distal extremity of the body having a chamfer formed thereon, said helical thread extending over said chamfer.

2. A device as in claim 1 wherein said first outer cylindrical surface extends for a distance from the distal extremity of the integral body to the proximal extremity of the first outer cylindrical surface which is greater than one-half the distance from the distal extremity of the integral body to the proximal extremity of the second outer tapered surface.

3. A device as in claim 1 wherein said outer surface has a taper ranging from 15°–30°.

4. A device as in claim 1 together with means carried by the body adapted to be engaged by the fingers of the hand so the fingers of the hand can be utilized for rotating the body to advance the body into the incision.

5. A skin seal device assembly for making a substantially gas-tight seal with the skin of a patient having a wall with an incision therein and for receiving an introducer comprising an integral body having proximal and distal extremities and having a flow passage extending from the proximal to the distal extremity, said body having a first outer cylindrical surface extending from the distal extremity toward the proximal extremity and having a substantially uniform diameter and a second outer tapered surface extending from the first surface toward the proximal extremity and having a gradually increasing diameter, a continuous helical thread of the same number of threads per inch for the first outer cylindrical surface and the second outer tapered surface without a discontinuity formed on the first and second outer surfaces extending from the distal extremity towards the proximal extremity and means carried by the proximal extremity of the body for receiving the introducer to have the same extend through the body and movable between releasing and engaging positions with respect to the introducer, said distal extremity of said body being provided with a chamfer, said thread commencing on said chamfer and extending over said chamfer.

* * * * *